(12) United States Patent
Schreiber (10) Patent No.: US 9,091,680 B1
(45) Date of Patent: Jul. 28, 2015

(54) FECAL OCCULT BLOOD TESTING SYSTEM

(71) Applicant: Robert Schreiber, Chestertown, MD (US)

(72) Inventor: Robert Schreiber, Chestertown, MD (US)

( * ) Notice: Subject to any disclaimer, the term of this patent is extended or adjusted under 35 U.S.C. 154(b) by 0 days.

(21) Appl. No.: 14/282,458

(22) Filed: May 20, 2014

(51) Int. Cl.
*C12Q 1/04* (2006.01)
*C12M 1/00* (2006.01)
*G01N 33/50* (2006.01)

(52) U.S. Cl.
CPC .................................. *G01N 33/5091* (2013.01)

(58) Field of Classification Search
CPC .................................. C12Q 1/04; C12M 1/00
USPC .................................................. 435/34, 283.1
See application file for complete search history.

(56) References Cited

U.S. PATENT DOCUMENTS

| | | | |
|---|---|---|---|
| 3,802,842 A | 4/1974 | Lange et al. | |
| 4,859,612 A | 8/1989 | Cole et al. | |
| 5,078,968 A | 1/1992 | Nason | |
| 5,171,529 A | 12/1992 | Schreiber | |
| 5,183,742 A | 2/1993 | Omoto et al. | |
| 5,264,181 A | 11/1993 | Schreiber | |
| 5,712,170 A | 1/1998 | Kouvonen et al. | |
| 5,739,041 A | 4/1998 | Nazareth et al. | |
| 5,766,962 A * | 6/1998 | Childs et al. | 436/518 |
| 6,248,294 B1 | 6/2001 | Nason | |
| 6,565,808 B2 | 5/2003 | Hudak et al. | |
| 6,767,714 B2 | 7/2004 | Nazareth et al. | |
| 7,045,342 B2 | 5/2006 | Nazareth et al. | |
| 7,264,776 B2 | 9/2007 | Guo et al. | |
| 7,326,578 B2 | 2/2008 | Bateman et al. | |
| 7,338,634 B2 | 3/2008 | Chang | |
| 7,544,324 B2 * | 6/2009 | Tung et al. | 422/504 |
| 7,622,729 B2 | 11/2009 | Duesbury | |
| 7,763,454 B2 | 7/2010 | Nazareth et al. | |
| 7,772,578 B2 | 8/2010 | Duesbury et al. | |
| 7,776,618 B2 | 8/2010 | Nazareth et al. | |
| 7,780,915 B2 | 8/2010 | Gao | |
| 7,794,656 B2 | 9/2010 | Liang et al. | |
| 7,799,275 B2 | 9/2010 | Duesbury et al. | |
| 7,837,939 B2 | 11/2010 | Tung et al. | |
| 7,871,568 B2 | 1/2011 | Liang et al. | |
| 8,053,203 B2 | 11/2011 | Wan et al. | |
| 8,062,901 B2 | 11/2011 | Dai et al. | |
| 8,211,711 B2 | 7/2012 | Nazareth et al. | |
| 8,216,832 B2 | 7/2012 | Battrell et al. | |
| 8,268,636 B2 | 9/2012 | Nazareth et al. | |
| 8,278,109 B2 | 10/2012 | Nazareth et al. | |
| 8,431,405 B2 | 4/2013 | Nazareth et al. | |
| 8,449,835 B2 | 5/2013 | Wu | |
| 8,623,635 B2 | 1/2014 | Nazareth et al. | |
| 2002/0042082 A1 | 4/2002 | Nazareth et al. | |
| 2004/0063219 A1 | 4/2004 | Bateman et al. | |
| 2004/0171174 A1 | 9/2004 | Nazareth et al. | |
| 2006/0008896 A1 | 1/2006 | Nazareth et al. | |
| 2008/0213920 A1 | 9/2008 | Nazareth et al. | |
| 2008/0227208 A1 | 9/2008 | Yee et al. | |
| 2008/0286831 A1 | 11/2008 | Liang | |
| 2009/0215159 A1 | 8/2009 | Kirby | |
| 2010/0239460 A1 | 9/2010 | Nazareth et al. | |
| 2010/0240149 A1 | 9/2010 | Nazareth et al. | |
| 2010/0261293 A1 | 10/2010 | Nazareth et al. | |
| 2010/0267166 A1 | 10/2010 | Nazareth et al. | |
| 2010/0311188 A1 | 12/2010 | Nazareth et al. | |
| 2011/0201122 A1 | 8/2011 | Nazareth et al. | |
| 2012/0083044 A1 | 4/2012 | Sturman et al. | |
| 2012/0083047 A1 | 4/2012 | Nazareth et al. | |
| 2012/0315656 A1 | 12/2012 | Nazareth et al. | |
| 2013/0157379 A1 | 6/2013 | Nazareth et al. | |
| 2013/0164858 A1 | 6/2013 | Nazareth et al. | |

FOREIGN PATENT DOCUMENTS

WO  2013158504 A1  10/2013

OTHER PUBLICATIONS

AxonLab, "iColo-Rectal Test" (date unknown—admitted prior art).

* cited by examiner

*Primary Examiner* — Karen Cochrane Carlson
*Assistant Examiner* — Natalie Moss
(74) *Attorney, Agent, or Firm* — Panitch Schwarze Belisario & Nadel LLP (57) ABSTRACT

A fecal occult blood testing system includes a testing unit that has an initial storage chamber, a secondary storage/mixing chamber, a window, a test strip viewable through the window, a vial containing analyte disposed within the testing unit, and a specimen collector. Prior to testing, the specimen collector may be positioned within the initial storage chamber. After specimen collection, the specimen collector is positioned within the secondary storage/mixing chamber. The tip of the specimen collector pierces a sealing cap on the vial so that the collected specimen mixes with the analyte in a channel formed in the testing unit. Once the specimen and analyte mixture is formed, the test strip absorbs and wicks the mixture to the test strip. The test strip detects and indicates, when viewed through the window, the presence or absence of fecal occult blood.

13 Claims, 7 Drawing Sheets

FECAL OCCULT BLOOD TESTING SYSTEM

BACKGROUND

1. Field of the Invention

The field of the invention relates to fecal occult blood testing systems.

2. Background

The presence of fecal occult blood, i.e. fecal matter blood, which is not visibly apparent, can indicate various types of illnesses. For example, occult blood can indicate digestive system irritation, growths or polyps in the colon or rectum, hemorrhoids, anal fissures, ulcers, and intestinal infections which cause inflammation. The detection of occult blood is also useful for screening various cancers, particularly colon and colorectal cancers.

There are two known types of occult blood tests for feces: (a) Fecal Occult Blood Testing (FOBT) using a chemical such as guaiac; and (b) Fecal Immunoglobin Testing (FIT) using an antihuman antibody.

For screening purposes, in particular, it is very important to facilitate the detection of occult blood. The ability for patients to test for occult blood on their own—without assistance from a laboratory or a medical professional—can make detection easier. To this end, several attempts have been made to develop testing devices and systems a patient can use in privacy to detect fecal occult blood.

Unfortunately, many traditional home testing devices and systems are not very user-friendly. And many of these devices and systems make proper collection of feces specimens difficult. Some devices, for example, require more precise positioning and sampling of feces specimens. Other devices are used with collection sticks, which are not contained within the testing device. Although, collection sticks are usually sealed before use, it is possible that a patient may contaminate a collection stick before specimen collection occurs. A patient also may inadvertently collect an excess amount of specimen. Traditional testing devices and systems, however, do not provide a way to remove excess specimen before application.

For these reasons, among others, there is a need for improved test systems that detect occult blood in fecal matter. The present invention fulfills this need and provides further related advantages, as described in the following summary.

SUMMARY

A fecal occult blood testing system includes a testing unit that has an initial storage chamber, a secondary storage/mixing chamber, a window, a test strip viewable through the window, a vial disposed within the testing unit, and a specimen collector. The specimen collector is configured for pre-use positioning within the initial storage chamber. The specimen collector is removed from the initial storage chamber and its bristles or other receiving structure are loaded with specimen (such as fecal matter). After collection of the specimen, the specimen collector is inserted into the secondary storage/mixing chamber. Upon such insertion into the storage/mixing chamber, the specimen collector pierces a sealing cap on the vial such that the collected specimen mixes with an analyte contained in the vial. Once the specimen and analyte mixture is formed, it is expressed through a channel onto the test strip which absorbs and wicks the mixture to facilitate lateral flow of the mixture to the test strip. The test strip will thereafter detect and indicate, when viewed through the window, the presence or absence of fecal occult blood.

BRIEF DESCRIPTION OF THE DRAWINGS

The drawings described herein are for illustrative purposes only and not intended to limit the scope of the present disclosure.

DETAILED DESCRIPTION

Figure 2:
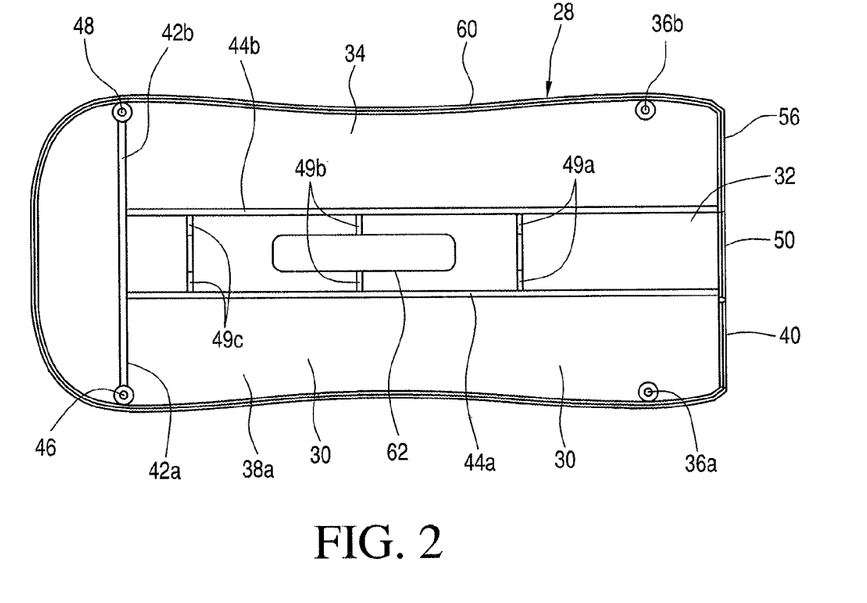
FIG. 2 shows the interior structure of an upper housing of the testing unit.
Figure 3:
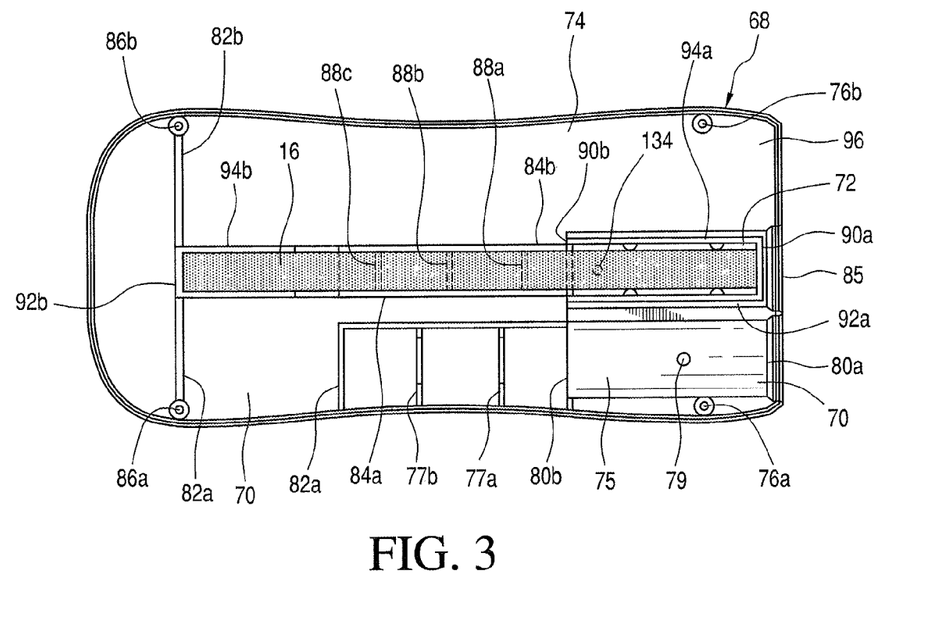
FIG. 3 shows the interior structure of a lower housing of the testing unit.
Figure 4:
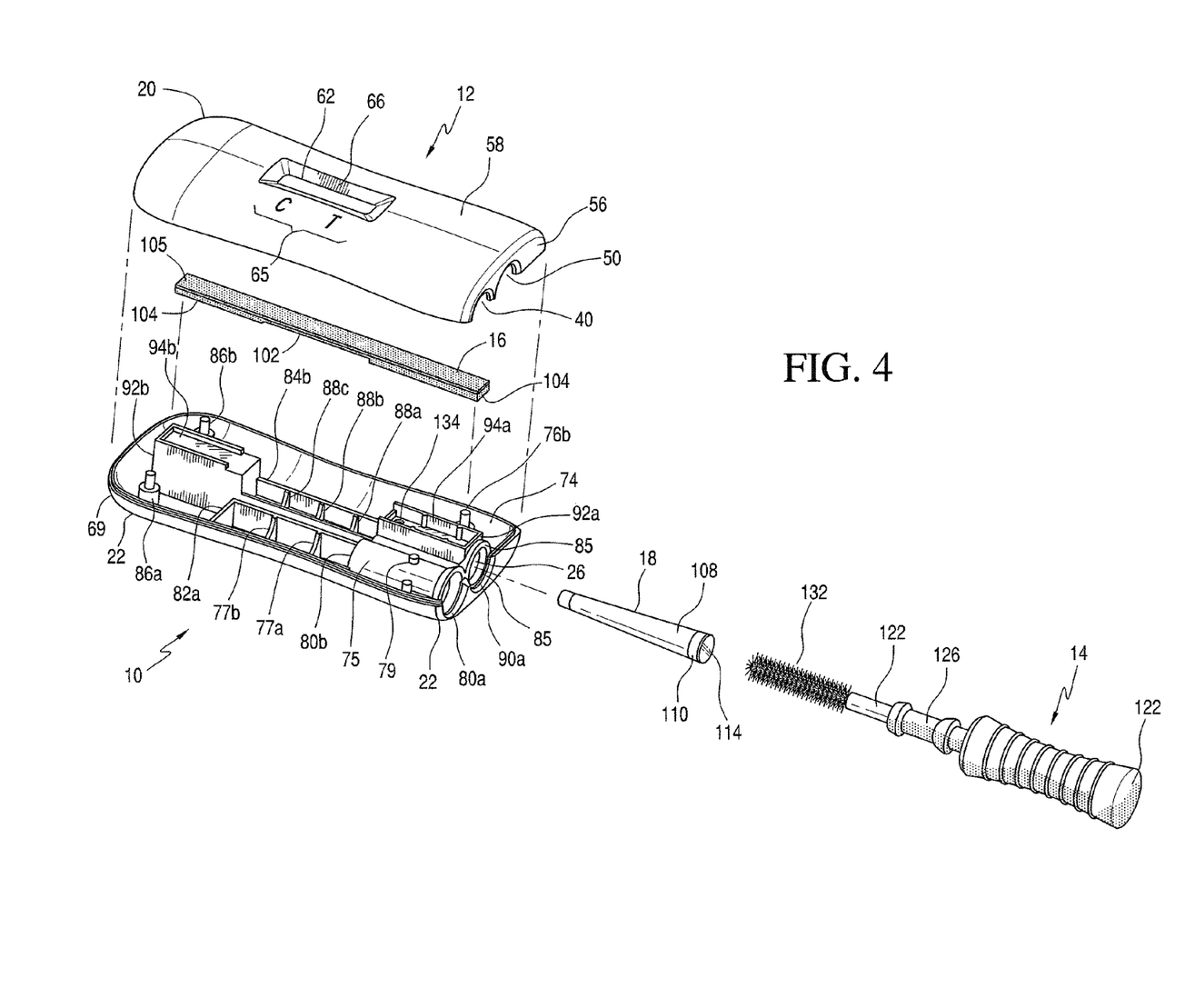
FIG. 4 is an exploded view of the testing system shown in FIGS. 1A-1C.

Turning in detail to the drawings, FIGS. 1A-8 show one embodiment of a testing system 10, which is used for fecal occult blood detection. This embodiment of the system 10 includes a testing unit 12, a specimen collector 14, a test strip 16, and a vial 18 (FIGS. 4 and 6-8). FIGS. 1A-1C and 5-8 show the testing system 10 at various stages of use, while FIG. 4 shows an exploded view of the testing system 10 before use.

As particularly shown in FIG. 4, the testing unit 12 is manufactured from one or more moldable polymeric (e.g., plastic) materials to include an upper housing 20 and a lower housing 22. These housings 20, 22 include complementary interior structures such that upon mating of the housings, an initial storage chamber 24 and a secondary storage/mixing chamber 26 for the specimen collector are formed. These chambers 24, 26 are used to facilitate proper collection of a feces specimen, as further described below. The testing unit 12 has particular efficacy for FIT testing.

FIG. 2 shows an upper housing interior structure 28. This configuration of the upper housing interior structure 28 includes three sections: (1) an initial storage chamber upper section 30, (2) a secondary storage chamber upper section 32, bounded to form a substantially T-shape, and (3) an upper unit mating section 34.

The initial storage chamber upper section 30 includes a front upper mating element 36a, a contoured inner surface 38a, and a semi-circular open end 40. This section is further bounded by a first upper rear wall 42a and a first upper inner wall 44b. Optionally, this chamber 30 can include ridges or serrations (not shown in FIG. 2), which may be used to remove excess fecal matter from a collector before testing.

The secondary storage chamber upper section 32 is bounded also by the first upper rear wall 42a and the first upper inner wall 44a. Included within the secondary storage chamber upper section 32 are rear upper mating elements 46, 48, and upper housing gussets 49a, 49b, 49c positioned respectively near the front, middle, and rear of the section 32. The secondary storage chamber upper section 32 is further bounded by the second upper rear wall 42b and the second upper inner wall 44b. This section also includes a semi-circular open end 50.

Walls 42b, 44b further bound the upper unit mating section 34, along with the front upper wall 56. The upper unit mating section 34 includes a contoured inner surface 38b and a front upper mating element 36b, like the initial storage chamber upper section 30.

Figures 1A, 1B, 1C:
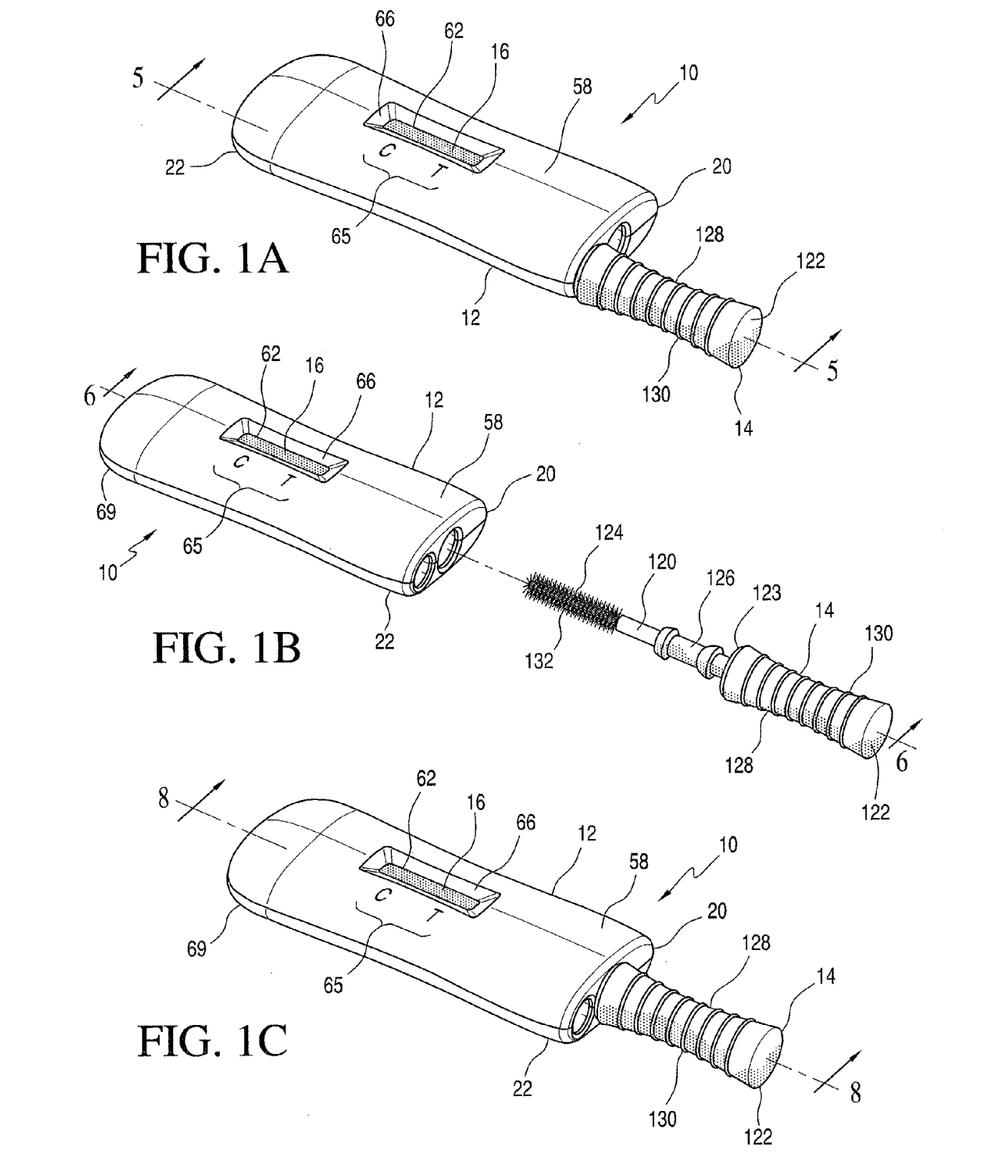
FIG. 1A shows a perspective view of a fecal occult blood testing system with a specimen collector positioned within an initial storage chamber.
FIG. 1B shows a perspective view of the testing system shown in FIG. 1A with the specimen collector aligned for insertion into a secondary chamber.
FIG. 1C shows the testing system shown in FIG. 1A with the specimen collector inserted into the secondary storage chamber.

A window 62 is positioned within the upper housing 20 for viewing of the test strip 16 (See FIGS. 1-3). Preferably, the window 62 is, positioned centrally within the upper housing 20. The window 62 extends fully through to the exterior surface 58 (FIGS. 1-3) of the upper section 20. The exterior surface 58 may include indicia 65 and a chamfered border 66 positioned around the window 62.

With the exception of the front section 64 of the upper housing, including open ends 40, 50 and the front upper wall, the upper housing interior structure 28 is bounded by an upper housing perimeter wall 60 that extends around the periphery of the upper housing 20.

FIGS. 3 and 4 show the lower housing interior structure 68. Like the upper housing interior structure 28, the lower housing interior structure 68 includes sections: (1) an initial storage chamber lower section 70, (2) a secondary storage chamber lower section 72, bounded to form a substantially T-shape, and (3) a lower unit mating section 74.

The initial storage chamber lower section 70 includes an initial specimen collector conduit 75, a front lower mating element 76a, and a contoured inner surface 78a. Also as shown particularly in FIG. 4, this section may include gussets 77a, 77b, and the conduit 75 may include a pin 79 on its outer surface to facilitate mating of the lower and upper housings. The conduit also includes circular open ends 80a, 80b. This section is bounded by a first lower rear wall 82a and a first lower inner wall 84a.

The secondary storage chamber lower section 72 is bounded by the first lower rear wall 82a and the first lower inner wall 84a. Included within the secondary storage chamber lower section 72 are a secondary specimen collector conduit 85, rear lower mating elements 86a, 86b, and lower housing gussets 88a, 88b, 88c positioned respectively near the front, middle and rear of the secondary storage chamber lower section 72. The collector conduit 85 includes open ends 90a, 90b and a test strip end holders 92a, 92b. Defined within these holders are recesses 94a, 94b, which are configured for secure placement of the ends of a test strip 16, as shown in FIG. 3.

Walls 82b, 84b further bound the lower unit mating section 74, along with the front lower wall 96. The lower unit mating section 74 includes a contoured inner surface 78b and a front mating element 76b.

Both the exterior surface 58 of the upper housing and the exterior surface 69 of the lower housing are contoured such that upon mating the testing unit fits comfortably in a normal-sized hand. Preferably, both the upper and lower housings are molded from polymeric materials, most preferably from one or more thermoplastic materials. These materials may contain one or more resins, such as polyvinylchloride (PVC), poly-ethylene (PE), polyethylene terephthalate (PET), polyoxymethylene (POM), polyamides (nylon), polypropylene, ethylene vinyl acetate, acrylonitrile butadiene styrene (ABS), and styrene-acrylonitrile, copolymers thereof, and mixtures thereof. Further, the resin composition preferably is mixed, blended, or compounded with additives, such as but not limited to pigments, colorants, or other particles, to form an injection moldable material.

FIGS. 4 and 6-8 show how the test strip 16 and the vial 18 containing analyte 112 are aligned and positioned within the testing system 10. The test strip 16 preferably includes at least one absorbent layer 102, a membrane layer 104, and a support layer 105. As shown in FIG. 4, two membrane layers 104 are connected by absorbent layer 102, and the support layer 105 is disposed adjacent the absorbent layer 102. Exemplary materials for the absorbent layer include, but are not limited to cellulose based materials, such as nitrocellulose, which incorporate one or more indicators of occult blood. Indicator types include, but are not limited to globulins, immunoglobulins, and gold conjugate. An exemplary material for the membrane layer is polyvinyl chloride (PVC). These layers 102, 104, 105 preferably are adhered together.

The vial 18 includes an outer vial housing 108 with an open vial end 110, an analyte 112 disposed within the housing, and a sealing cap 114 positioned over the open end 110. The outer vial housing 108 preferably has a cone-like shape or other shape that fits within the secondary storage/mixing chamber 26. The outer vial housing 108 may be formed of polymeric materials, such as but not limited to resins of thermoplastic materials, including polypropylenes, polyurethanes, polycarbonates, and polyethylenes. One preferred material for the outer vial housing 108 is polyethylene.

FIGS. 1A-1C and 4-8 show how the specimen collector 14 is aligned and positioned with the testing system 10. The collector 14 includes a shaft 120 having at its distal end a handle 122 with gripping elements 130 on its outer surface and a friction collar 123 adapted for contact with end surfaces of the housings 20, 22. The collector 14 further includes a plunger/piston 126 which forms a water-tight seal with the walls of the secondary chamber 72. At its proximal end, the collector 14 has a piercing tip 124.

Preferred materials for both the shaft 120 and the handle 122 include polymeric materials, such as but not limited to resins of thermoplastic materials, including polypropylenes, polyurethanes, polycarbonates, and polyethylenes. The plunger/piston 126 may be formed of silicone.

The tip 124 may be manufactured from a variety of materials and may be formed around the shaft to have various shapes. The tip may include a plurality of bristles 132, as shown in FIGS. 1B and 4-8. Other contemplated materials for the tip include conformable materials such as brush bristles, sponge-like materials, foam-based materials, and synthetic fiber materials. Exemplary fiber materials include those manufactured from acetate, aramide, polyamide, polyester, polyolefin, polyurethane, and mixtures thereof.

Figure 5:
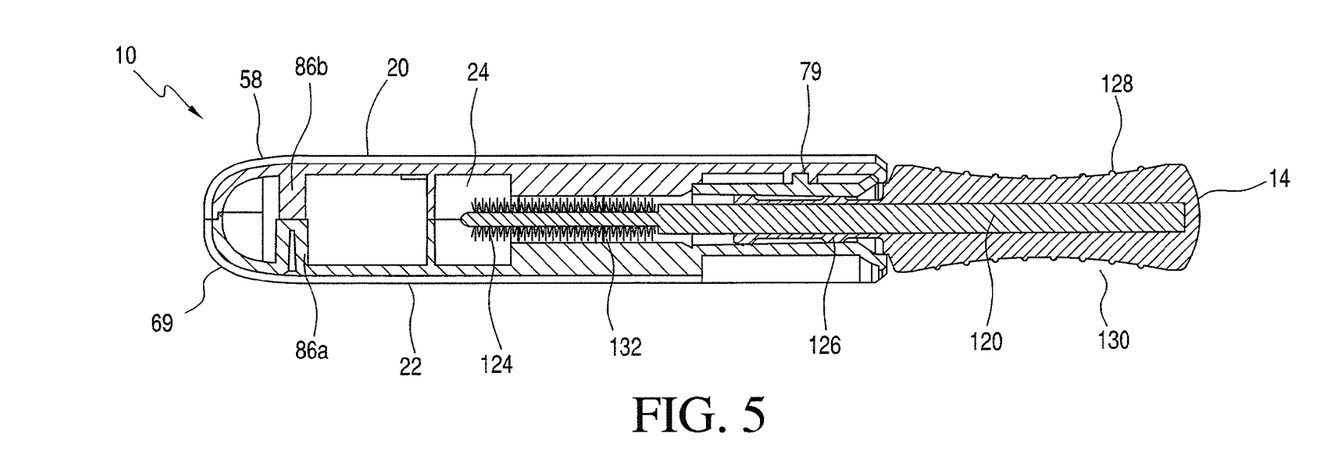
FIG. 5 is a cross-sectional view of the testing system shown in FIG. 1A, taken along line 5-5 of FIG. 1A.
Figure 6:
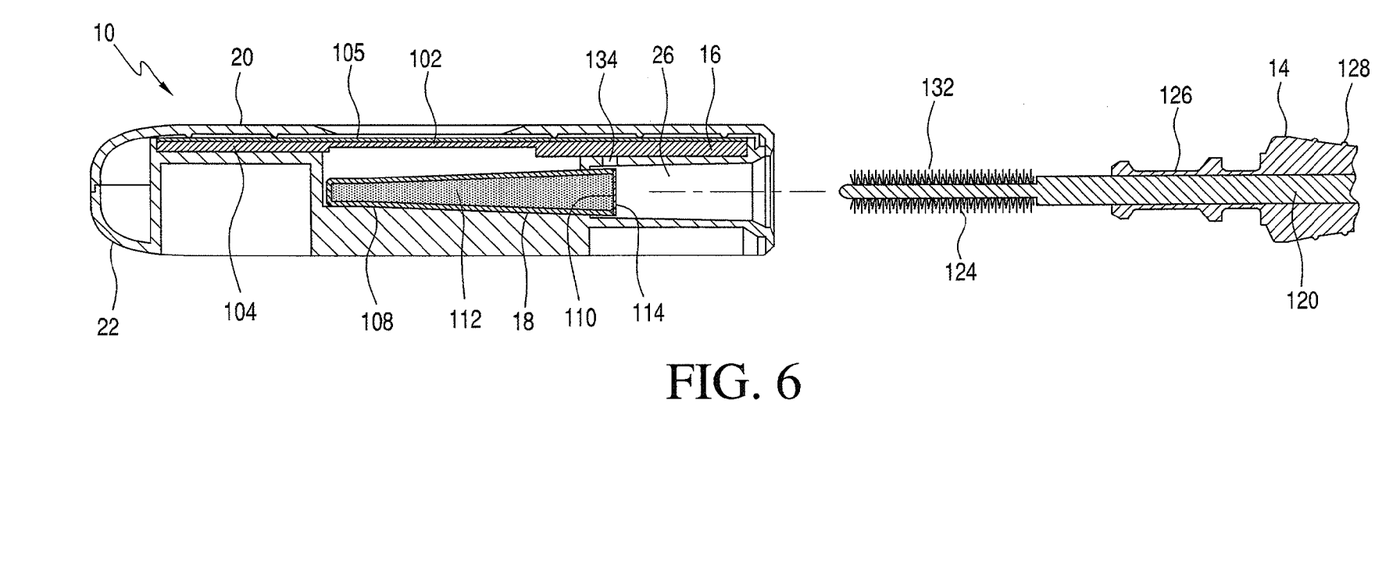
FIG. 6 shows a cross-sectional view of the testing system shown in FIG. 1B, taken along line 6-6 of FIG. 1B.
Figure 7:
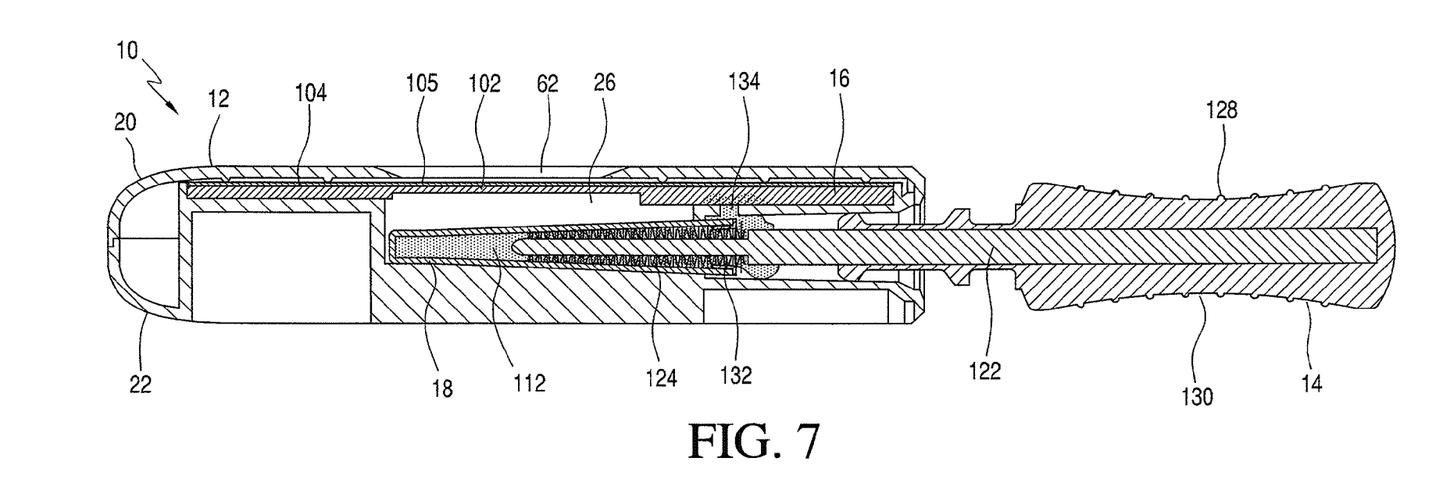
FIG. 7 shows a cross-sectional view of the testing system after initial insertion of the specimen collector.

As shown in FIGS. 1A and 5, the test system 10 preferably is packaged and sold with the specimen collector 14 positioned in the initial storage chamber 24 of the assembled testing unit 12. To use the system 10, a user removes the specimen collector 14 and inserts the tip 124 into fecal matter so that an amount of fecal matter specimen binds or sticks onto the tip. Thereafter, the user aligns the collector 14 with the secondary storage/mixing chamber 26, as shown in FIGS. 1B and 6, and inserts the tip 124 of the specimen collector 14 into the secondary storage/mixing chamber 26. The sealing cap 114 on the vial 18 is pierced by the tip 124 as the proximal end of the collector 14 is inserted into the vial 18, as shown in FIGS. 1C and 7. The collected specimen (not shown) mixes with the analyte 112 released from the vial 18. The mixture 136 of collected specimen and analyte 112 flows through a channel 134, which is formed upon assembly of the lower and upper housings 20, 22.

Figure 8:
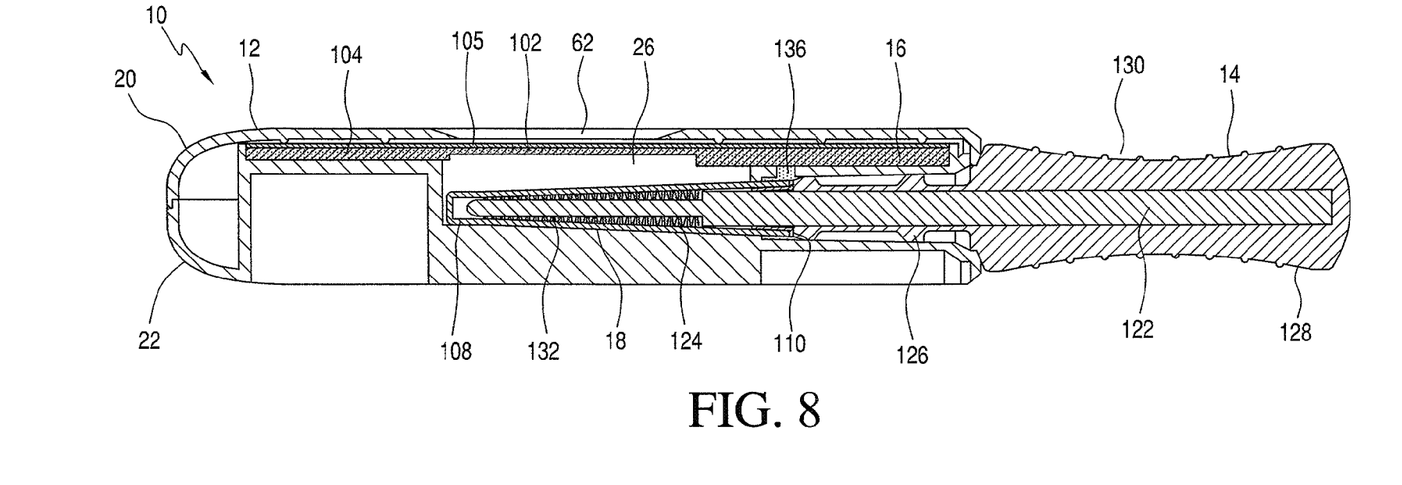
FIG. 8 shows a cross-sectional view of the testing system shown in FIG. 1C, taken along line 8-8 of FIG. 1C, after full insertion of the specimen collector.

The mixture 136 formed by the combination of the specimen and the analyte 112 is shown in FIG. 8. Once the mixture 136 is formed, the absorbent layer 102 absorbs the mixture and the membrane 104 wicks the mixture to facilitate lateral flow of the mixture to the test strip 16. The test strip 16 detects and indicates the presence or absence of fecal occult blood by indicia, such as color display or pattern, that is visible to the user through the window 62.

Figure 9:
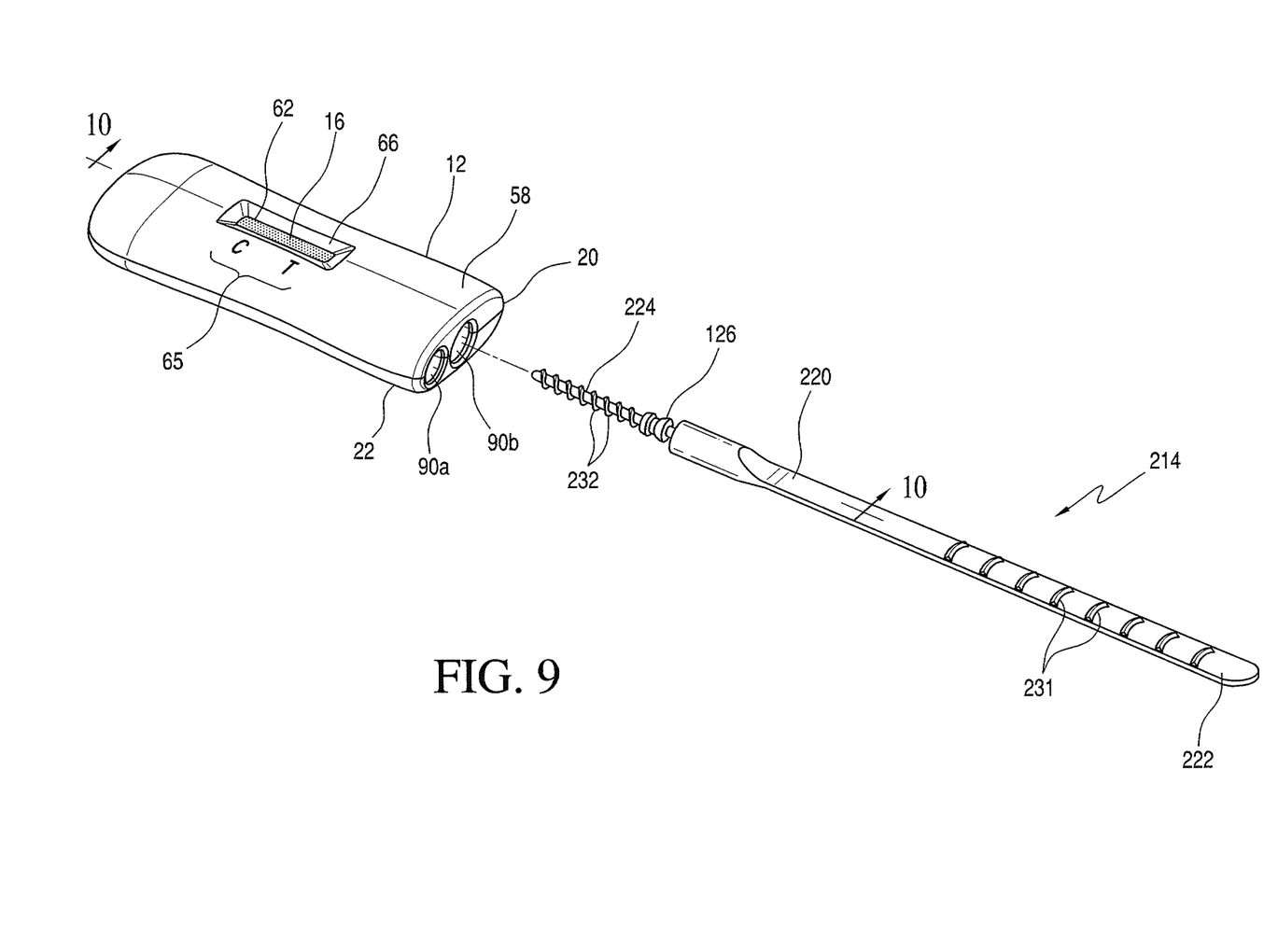
FIG. 9 shows a perspective view of an alternative embodiment of a fecal occult blood testing system with a different specimen collector.
Figure 10:
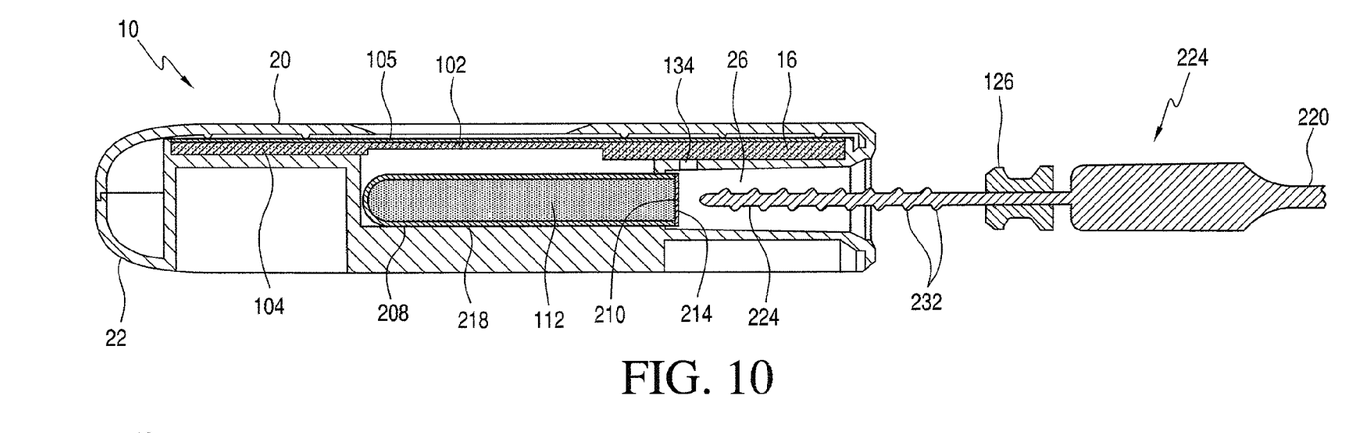
FIG. 10 shows a cross-sectional view of the testing system shown in FIG. 9 taken along line 10-10 of FIG. 9.
Figure 11:
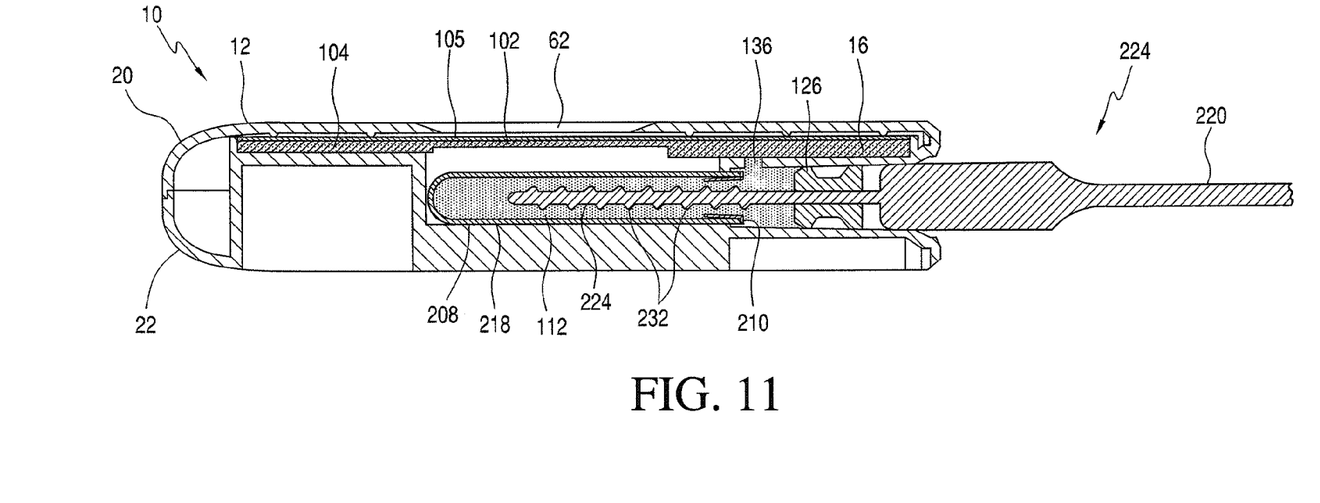
FIG. 11 shows a cross-sectional view of the testing system shown in FIG. 9 after full insertion of the specimen collector.

A second embodiment of the invention is shown in FIGS. 9-11. Like reference numerals refer to like structure between the first and second embodiments. In the second embodiment, the vial 218 includes an outer vial housing 208 with an open vial end 210, an analyte 112 disposed within the housing, and a sealing cap 214 positioned over the open end 210. The outer vial housing 208 preferably has a cylindrical shape with a curved bottom end that fits within the secondary storage/mixing chamber 26.

The specimen collector 214 has a distal end 222 with a plurality of gripping elements 231 spaced apart at or near the distal end 222. The specimen collector has a piercing tip 224 at its proximal end. The shaft 220 of the specimen collector 214 also has a series of specimen collection notches 232 or channels at or near the proximal end. When the proximal end of the specimen collector 214 contacts a stool specimen, some fecal material is held in the notches 232 or channels. The proximal end of the specimen collector 214 then is inserted into the secondary storage/mixing chamber 26 so that the piercing tip 224 of the specimen collector pierces the sealing cap 214 on the vial 218 to permit the fecal matter to mix with analyte 112 released from the vial 218.

The specimen collector 214 may be molded of a polymeric material or mixture of polymeric materials. Preferably, the specimen collector 214 is injection molded of the same or similar polymeric materials as form the upper and lower housings 20, 22. A plunger/piston 126 on the specimen collector 214 forms a water-tight seal with the walls of the secondary chamber 26.

While embodiments of this invention have been shown and described, it will be apparent to those skilled in the art that many more modifications are possible without departing from the inventive concepts herein. The invention, therefore, is not to be restricted except in the spirit of the following claims.

What is claimed is:

1. A fecal occult blood testing system, comprising:
a testing unit formed from an upper housing and a lower housing, said testing unit having a first storage chamber, a second storage chamber that also is a mixing chamber, and a window, wherein the lower housing comprises a first storage chamber lower section, a second storage chamber lower section and a lower unit mating section, and the first storage chamber lower section comprises an initial specimen collector conduit;
a test strip disposed within the testing unit and viewable through the window;
a vial positioned within the second storage chamber, the vial comprising an analyte for the detection of fecal occult blood; and
a specimen collector for collecting fecal matter, said specimen collector adapted for at least partial insertion into the first storage chamber as its pre-test position, and adapted for at least partial insertion into the second storage chamber as its test position,
wherein the specimen collector has a tip adapted to pierce the vial or a portion of the vial to release analyte for mixing with collected fecal matter specimen on the specimen collector when the specimen collector is inserted into the second storage chamber.

2. The testing system of claim 1, wherein the second storage chamber lower section comprises a secondary specimen collection conduit.

3. The testing system of claim 1, further comprising one or more test strip end holders.

4. The testing system of claim 2, comprising a test strip end holder positioned on top of the secondary specimen collection conduit.

5. The testing system of claim 1, wherein the specimen collector comprises a shaft, a handle positioned at the distal end of the collector, and the tip at the proximal end of the collector.

6. The testing system of claim 5, wherein the specimen collector comprises a plurality of stick bristles mounted at or near its proximal end.

7. The testing system of claim 5, wherein the specimen collector has a plurality of notches or channels at or near its proximal end.

8. The testing system of claim 5, wherein the vial further comprises a sealing cap and the tip of the specimen collector is adapted for piercing the sealing cap to release analyte from the vial.

9. The testing system of claim 1, further comprising means to remove excess fecal matter from the specimen collector.

10. A testing system, comprising:
a testing unit formed from an upper housing and a lower housing, said testing unit having a first storage chamber, a second storage chamber that also is a mixing chamber, and a window, wherein the lower housing comprises a first storage chamber lower section, a second storage chamber lower section and a lower unit mating section, and the first storage chamber lower section comprises an initial specimen collector conduit;
a test strip disposed within the testing unit and viewable through the window;
a vial positioned within the second storage chamber, the vial comprising an analyte; and
a specimen collector to collect specimen, said specimen collector adapted for at least partial insertion into the first storage chamber as its pre-test position and adapted for at least partial insertion into the second storage chamber as its test position,
wherein the specimen collector has a tip adapted to pierce the vial to release analyte for mixing with a collected specimen on the specimen collector when the specimen collector is inserted into the second storage chamber.

11. The testing system of claim 10, further comprising means to remove excess specimen from the specimen collector.

12. The testing system of claim 10, wherein the vial contains an analyte for the detection of blood.

13. The testing system of claim 10, wherein the specimen collector comprises either a plurality of bristles or a plurality of notches or channels at or near its proximate end adapted for collecting specimen material expelled from a patient.

* * * * *